(12) United States Patent
Li et al.

(10) Patent No.: US 10,328,122 B2
(45) Date of Patent: Jun. 25, 2019

(54) METHOD OF TREATING FULMINANT HEPATIC FAILURE USING DLL4 CYTOKINE

(71) Applicant: Zhejiang University, Hangzhou, Zhejiang (CN)

(72) Inventors: Jun Li, Zhejiang (CN); Lanjuan Li, Zhejiang (CN); Xin Chen, Zhejiang (CN); Jiang Li, Zhejiang (CN)

(73) Assignee: Zhejiang University, Hangzhou (CN)

( * ) Notice: Subject to any disclaimer, the term of this patent is extended or adjusted under 35 U.S.C. 154(b) by 56 days.

(21) Appl. No.: 15/367,239

(22) Filed: Dec. 2, 2016

(65) Prior Publication Data

US 2017/0080052 A1 Mar. 23, 2017

Related U.S. Application Data

(63) Continuation-in-part of application No. PCT/CN2016/075574, filed on Mar. 4, 2016.

(30) Foreign Application Priority Data

Sep. 15, 2015 (CN) .......................... 2015 1 0582307

(51) Int. Cl.
*A61K 38/16* (2006.01)
*A61K 38/17* (2006.01)
*A61K 9/00* (2006.01)

(52) U.S. Cl.
CPC ........ *A61K 38/1709* (2013.01); *A61K 9/0019* (2013.01)

(58) Field of Classification Search
None
See application file for complete search history.

(56) References Cited

U.S. PATENT DOCUMENTS

2008/0145442 A1* 6/2008 Yarmush ............. A61M 1/3472
424/520
2008/0194575 A1* 8/2008 Beraza ................. A61K 31/505
514/252.14

OTHER PUBLICATIONS

Liu et al. 2012. Z Gastroenterol. 50-K009.*
UniProtKB-Q9NR61, Oct. 1, 2000, downloaded Jun. 11, 2018.*

* cited by examiner

*Primary Examiner* — Shulamith H Shafer

(57) ABSTRACT

A method of treating fulminant hepatic failure in a subject, includes administering a therapeutically effective amount of a pharmaceutical composition to the subject, wherein the pharmaceutical composition comprises a DLL4 cytokine. A method of treating liver failure, sub-acute liver failure, chronic liver failure or acute-on-chronic liver failure in a subject, includes administering an therapeutically effective amount of a DLL4 cytokine to the subject.

6 Claims, 4 Drawing Sheets

Specification includes a Sequence Listing.

```
                        SEQUENCE LISTING

<160> NUMBER OF SEQ ID NOS: 1

<210> SEQ ID NO 1
<211> LENGTH: 498
<212> TYPE: PRT
<213> ORGANISM: Homo sapiens

<400> SEQUENCE: 1

Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
        195                 200                 205

Lys Pro Ala Glu Cys Leu Cys Arg Pro Gly Trp Gln Gly Arg Leu Cys
    210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
        275                 280                 285

Gly Tyr Thr Gly Val Asp Cys Glu Leu Glu Leu Ser Glu Cys Asp Ser
    290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
                325                 330                 335
```

-continued

```
Thr Leu Ser Cys Ala Asp Ser Pro Cys Phe Asn Gly Gly Ser Cys Arg
            340             345             350

Glu Arg Asn Gln Gly Ala Asn Tyr Ala Cys Glu Cys Pro Pro Asn Phe
        355             360             365

Thr Gly Ser Asn Cys Glu Lys Lys Val Asp Arg Cys Thr Ser Asn Pro
    370             375             380

Cys Ala Asn Gly Gly Gln Cys Leu Asn Arg Gly Pro Ser Arg Met Cys
385             390             395             400

Arg Cys Arg Pro Gly Phe Thr Gly Thr Tyr Cys Glu Leu His Val Ser
            405             410             415

Asp Cys Ala Arg Asn Pro Cys Ala His Gly Gly Thr Cys His Asp Leu
        420             425             430

Glu Asn Gly Leu Met Cys Thr Cys Pro Ala Gly Phe Ser Gly Arg Arg
        435             440             445

Cys Glu Val Arg Thr Ser Ile Asp Ala Cys Ala Ser Ser Pro Cys Phe
    450             455             460

Asn Arg Ala Thr Cys Tyr Thr Asp Leu Ser Thr Asp Thr Phe Val Cys
465             470             475             480

Asn Cys Pro Tyr Gly Phe Val Gly Ser Arg Cys Glu Phe Pro Val Gly
            485             490             495

Leu Pro
```

METHOD OF TREATING FULMINANT HEPATIC FAILURE USING DLL4 CYTOKINE

CROSS REFERENCE TO RELATED APPLICATIONS

This application is a continuation-in-part application of PCT Application No. PCT/CN2016/075574 filed on Mar. 4, 2016, which claims priority to Chinese Patent Application No. 201510582307.1 filed on Sep. 15, 2015, the entire contents of which are incorporated herein by reference.

REFERENCE TO SEQUENCE LISTING

The Sequence Listing is submitted as an ASCII formatted text file via EFS-Web, with a file name of "Sequence_listing ZZZHCH-1603-USPT.TXT", a creation date of Sep. 13, 2018, and a size of 4,669 bytes. The Sequence Listing filed via EFS-Web is part of the specification and is incorporated in its entirety by reference herein.

FIELD OF TECHNOLOGY

The present application relates to the field of clinical, molecular and regenerative medicine. Particularly, the present application relates to a method of rescuing liver failure using a series of DLL4 cytokine drugs.

BACKGROUND

Fulminant hepatic failure (FHF) is a severe disease caused by varies etiologies and characterized by large area of liver necrosis. FHF patients mostly die over a short period of time. FHF patients treated by standard comprehensive medical therapy have more than 80% mortality. Currently, orthotropic liver transplantation is the only effective treatment and no other specific treatments are effective. Owing to the shortage of donor liver, many patients on the waiting list die before receiving the liver transplantation. It would be of great significance in the treatment of FHF caused by varies etiologies to find one or more cytokines which could suppress liver necrosis, rapidly induce host's liver tissue regeneration, function for a long period of time, and avoid potential side-effect. DLL4 cytokine is a type 1 transmembrane protein positioned on the cell membrane, which can act as a ligand to specifically activate Notch 1 and Notch 4 receptors.

Currently, DLL4 cytokine is often reported in the research areas of neoplastic disease, angiogenesis related disease, and cell proliferation and apoptosis.

SUMMARY

In view of the deficiency of existing technology, the present application provides a method of treating FHF using DLL4 cytokine.

The present application provides a method of treating fulminant hepatic failure in a subject, including administering a therapeutically effective amount of a pharmaceutical composition to the subject, wherein the pharmaceutical composition includes a DLL4 cytokine.

In an embodiment of the present application, the pharmaceutical composition further comprises a pharmaceutically acceptable excipient, an antioxidant and/or a carrier.

In an embodiment of the present application, the pharmaceutical composition is in a form of an injection, a lyophilized powder injection or an injectable suspension.

In an embodiment of the present application, the pharmaceutical composition has a storage and transportation temperature between 2° C. and 8° C., and a humidity between 45% and 75%.

In an embodiment of the present application, the pharmaceutical composition has a storage and transportation temperature between 15° C.-30° C., and a humidity between 45%-75%.

The present application also provides a method of treating liver failure, sub-acute liver failure, chronic liver failure or acute-on-chronic liver failure in a subject, including administering a therapeutically effective amount of a DLL4 cytokine to the subject.

Comparing to the existing technology, the benefits of the present application are as follows:

Based on researches on various aspects including biochemical index, immunohistochemistry, gene expression level and proteomics, the inventors of the present application discovered that DLL4 cytokine is effective in rescuing FHF. DLL4 cytokine may be combined with different solvents and stabilizers to produce various forms and doses of pharmaceutical composition. The pharmaceutical composition may be administered by intravenous injection or intramuscular injection.

DLL4 cytokine may overcome the problem that although hepatocytes regenerate during the course of FHF, the new proliferating hepatocytes could not survive for long and perform their function stably owing to the damage of the bile duct system. DLL4 cytokine may have an important role in the process of liver restoration via DLL4-Notch pathway activation. Meanwhile, DLL4 cytokine may act together with other cytokines in the Notch pathway to contribute to repair of the biliary duct. DLL4 cytokine may improve blood circulation in the diseased liver by inducing liver vascular endothelial cell proliferation and promoting angiogenesis. Also, DLL4 cytokine may regulate the immune response of patients and alleviate the immune injury. DLL4 may alleviate hepatocytes degeneration, apoptosis and necrosis, and suppress large area of liver necrosis. DLL4 cytokine may rapidly alter the immune response of individuals with hepatic failure and suppress inflammation. DLL4 may adjust fibrocytes proliferation and suppress large-scale synthesis of fibrin. DLL4 cytokine may significantly alleviate the degree of fibrosis during the regenerative process of the liver, and avoid cirrhosis. The method of treating FHF using DLL4 may significantly ameliorate the biochemical index of the patient, reduce the level of bilirubin and transaminase, improve blood coagulation, increase the level of albumin, induce hepatocytes and bile ducts regeneration, prevent the occurrence of severe complication (such as upper gastrointestinal hemorrhage, hepatic encephalopathy and hepatorenal syndrome) and significantly improve survival time and survival rate of the patients.

Beside the significant increase in survival rate in FHF therapy, DLL4 cytokine medicine may also significantly improve prognosis and increase survival rate in other severe hepatic diseases or end stage hepatic diseases having disease basis, progression and prognosis similar to FHF.

DETAILED DESCRIPTION

Figure 1:
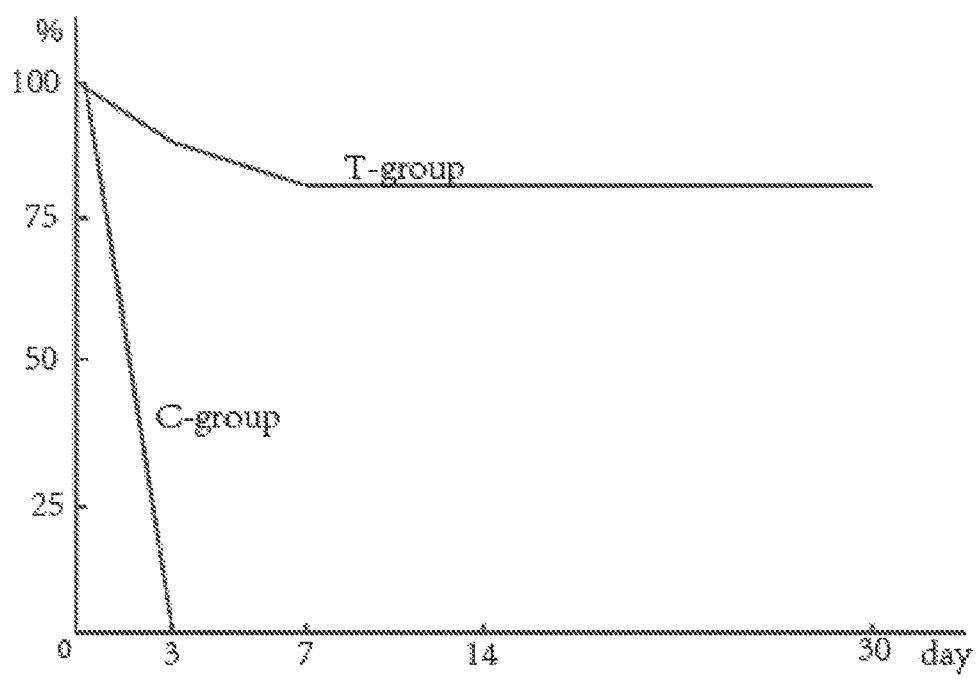
FIG. 1 is a survival curve of FHF treatment group and control group of piglets.

The present application provides a method of treating FHF using a pharmaceutical composition including human DLL4 cytokine as set forth in SEQ ID NO: 1. Different forms of the pharmaceutical composition will now be described in detail with reference to the specific embodiments as follows:

1. The injection including DLL4 cytokine:
1) Add 9 g NaCl to 1 liter distilled water.
2) Add 0.009 mg Tween-80 to half of the total volume of the step 1 solution.
3) Add 80 ml gelofusine to the step 2 solution.
4) Add proscribed dose of DLL4 cytokine to the step 3 solution.
5) Adjust the pH value to be 5.0-7.0 with 0.1 mol/L HCl.
6) Add 0.9% NaCl solution to the step 5 solution until reaching a constant volume (IL).
7) Subpackage and store the step 6 solution (transportation and storage temperatures: 2-8° C., humidity: 45%-75%, preferably, transportation and storage temperatures: 4° C.; during use, temperature: 15-30° C., humidity: 45%-75%).

2. The lyophilized powder injection including DLL4 cytokine:
1) Prepare sufficient volume of distilled water.
2) Completely dissolve DLL4 cytokine and proppants (mannitol, sorbitol, dextran, etc.) in a ratio of 1:5 in distilled water.
3) Adjust the pH value of the step 2 solution to be between 5.0-7.0 with 0.1 mol/L HCl.
4) Put the step 3 solution into freeze dryer: −40° C. freezing for 6 hours, −40° C. vacuum freezing for 24 hours: 20° C. drying for 2 hours.
5) subpackage and store the step 4 lyophilized powder (transportation and storage temperatures: 2-8° C., humidity: 45%-75%, preferably, transportation and storage temperatures: 4° C.; during use, temperature: 15-30° C., humidity: 45%-75%)

3. The injectable suspension including DLL4 cytokine (1000 ml):
1) Smash 100 g DLL4 cytokine to granules (5-10 μm).
2) Dissolve 30 g polyvinylpyrrolidone (PVP) in 1000 ml distilled water to form a solution.
3) ADD the step 1 granules to the step 2 solution.
4) Adjust pH value to be 6.0-7.0 with dilute HCL solution and dilute NaOH solution.
5) Mix the step 4 injectable suspension in high speed mixer for 1 hour (3500 r/min).
6) subpackage and store the step 5 injectable suspension (transportation and storage temperatures: 2-8° C., humidity: 45%-75%, preferably, transportation and storage temperatures: 4° C.; during use, temperature: 15-30° C., humidity: 45%-75%).

Specific embodiments of the present application will now be described in detail with reference to the accompanying drawings, examples and comparative examples:

In the present application, the experimental results of different animal models showed that pharmaceutical composition of DLL4 cytokine could significantly alleviate the degree of liver degeneration, ameliorate biochemical index, prolong survival time and improve survival rate. Hence, DLL4 cytokine is a promising medicine in FHF therapy and provide treatment of severe liver diseases.

Example 1. Injection Including DLL4 Cytokine for Rescuing FHF in Large Animal (Piglet) Model Animal model: 30 male Chinese experiment piglets (8-10 kg) were randomized into 2 groups with 15 piglets in each group. Each piglet received a dose of 1.5/kg D-gal injection through jugular vein to establish the FHF model.

Treatment group: multiple doses of DLL4 injection were given to the piglets at set time.

Dose: 10 ml/kg; twice a day.

Control group: the same dose of normal saline (without DLL4) was given to the piglets.

Both treatment group and control group did not receive other therapy.

FIG. 1 is the survival curve of piglets in treatment group and control group, showing the survival rate of both groups. The survival rate of treatment group who received the pharmaceutical composition of DLL4 cytokine was 93% at day 3, 85% at day 7, 85% at day 14, and the survival rate achieved long term stability. Meanwhile, all piglets in the control group died within 72 hours with an average survival time of 46 hours. Therefore, the pharmaceutical composition of DLL4 cytokine could significantly improve survival rate and survival time in rescuing FHF piglets compared to the control group. This shows that the present application has achieved apparent benefit.

Example 2. Lyophilized Powder Injection Including DLL4 Cytokine for Rescuing FHF in Small Animal (Rat) Model Animal model: 100 male rats weighed 200-250 g were randomized into 2 groups with 50 rats in each group. Each rats received a dose of 1.5 g/kg D-gal via intraperitoneal injection to establish the FHF model. The injection was prepared by forming a suspension using lyophilized powder and distilled water.

Treatment group: DLL4 lyophilized powder suspension was given to the rats at set time.

Dose: 4 ml; twice a day.

Control group: the same dose of normal saline (without DLL4) were given to the rats.

Both treatment group and control group did not receive other therapy.

Figure 2:
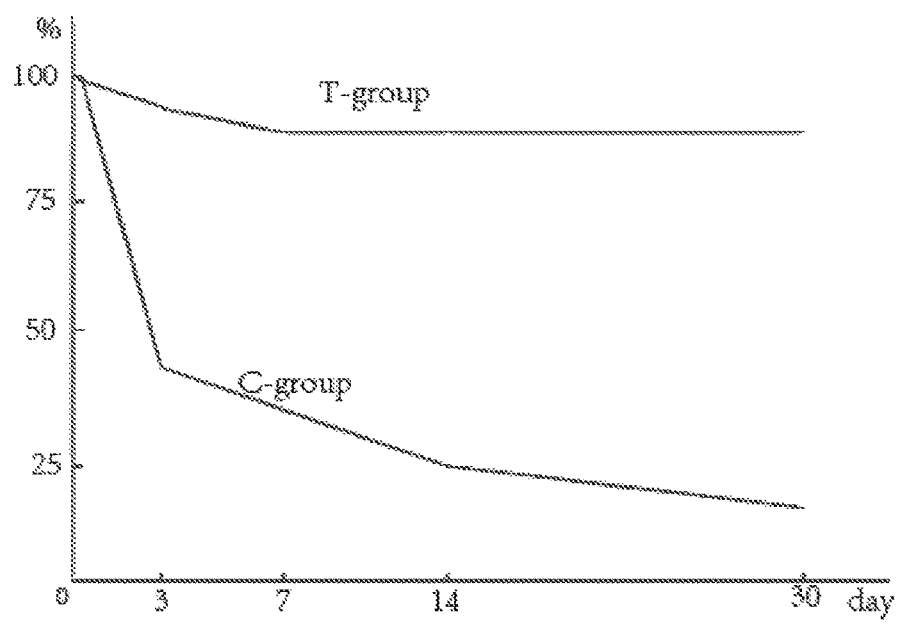
FIG. 2 is a survival curve of FHF treatment group and control group of rats.

FIG. 2 is the survival curve of rats in treatment group and control group, showing the survival rate of both groups. The survival rate of the rats in DLL4 treatment group was 96% at day 3, 94% at day 7, 94% at day 14. Meanwhile, the survival rate of control group was 24% at day 14. Therefore, the pharmaceutical composition of DLL4 cytokine could improve survival rate and survival time in rescuing FHF rats compared to the control group. This shows that the present application has achieved apparent benefit.

Example 3. Injectable Suspension Including DLL4 Cytokine for Rescuing FHF in Small Animal (Domestic Rabbit) Model Animal model: 40 male adult domestic rabbits weighed 2000-2500 g were randomized into 2 groups with 20 domestic rabbits in each group. Each domestic rabbits received a dose of 1.5 g/kg D-gal via intramuscular injection to establish the FHF model.

Treatment group: DLL4 suspension was given to the domestic rabbits at set time.

Dose: 20 ml; twice a day.

Control group: the same dose of normal saline (without DLL4) was given to the domestic rabbits.

Both treatment group and control group did not receive other therapy.

Figure 3:
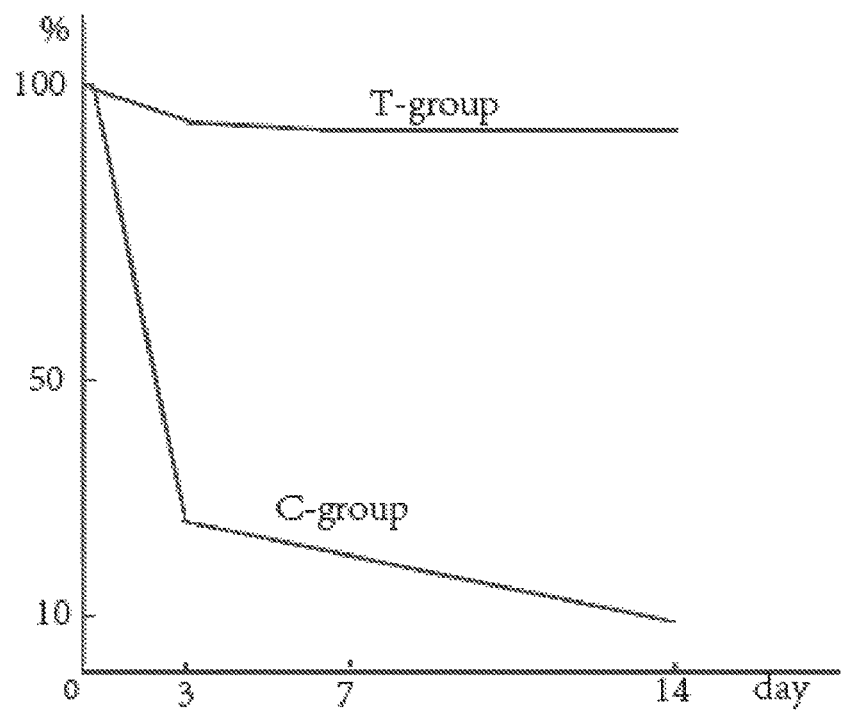
FIG. 3 is a survival curve of FHF treatment group and control group of domestic rabbits.

FIG. 3 is the survival curve of domestic rabbits in treatment group and control group, showing the survival rate of both groups. The survival rate of the domestic rabbits in the treatment group was 95% at day 3, 90% at day 7, 90% at day 14. Meanwhile, the survival rate of control group was 10% at day 14. Therefore, the pharmaceutical composition of DLL4 cytokine could improve survival rate and survival time in rescuing FHF domestic rabbits compared to the control group. This shows that the present application has achieved apparent benefit.

Example 4. Injectable Suspension Including DLL4 Cytokine for Rescuing FHF in Small Animal (Mouse) Model Animal model: 100 male mice weighed 20-25 g were randomized into 2 groups with 50 mice in each group. Each mouse received a dose of $CCl_4$ muscle injection to establish the FHF model.

Treatment group: DLL4 suspension was given to mice via intraperitoneal injection at set time.

Dose: 1 ml; twice a day.

Control group: the same dose of normal saline (without DLL4) was given to the mice.

Both Treatment group and Control group did not receive other therapy.

Figure 4:
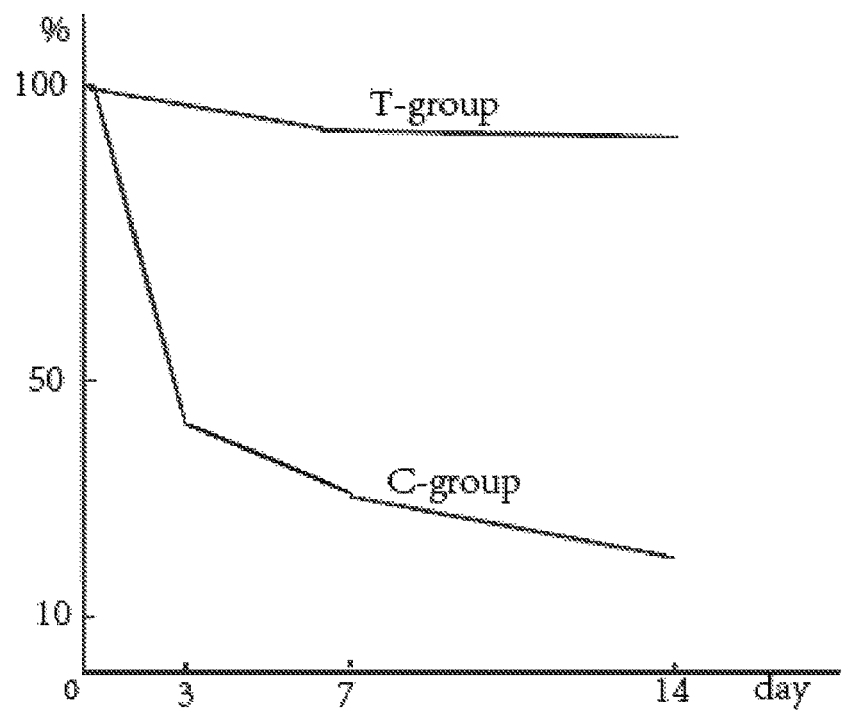
FIG. 4 is a survival curve of FHF treatment group and control group of mice.

FIG. 4 is the survival curve of mice in treatment group and control group, showing the survival rate of both groups. The survival rate of the mice in DLL4 treatment group was 98% at day 3, 94% at day 7, 92% at day 14. Meanwhile, the survival rate of the control group was 30% at day 14. Therefore, the pharmaceutical composition of DLL4 cytokine medicine could improve survival rate and survival time in rescuing FHF mice compared to control group. This shows that the present application has achieved apparent benefit.

Example 5. Lyophilized Powder Injection Including DLL4 Cytokine for Rescuing Sub-Acute Liver Failure in Small Animal (Rat) Model Animal model: 100 male rats weighed 200-250 g were randomized into 2 groups with 50 rats in each group. Each rat received a dose of 1.5 g/kg D-gal via intraperitoneal injection to establish the sub-acute liver failure model. The suspension was prepared with DLL4 lyophilized powder and distilled water.

Treatment group: DLL4 lyophilized powder suspension was given to rats via intraperitoneal injection at set time.
Dose: 4 ml; twice a day.

Control group: the same dose of normal saline (without DLL4) was given to the rats.

Both treatment group and control group did not receive other therapy.

Figure 5:
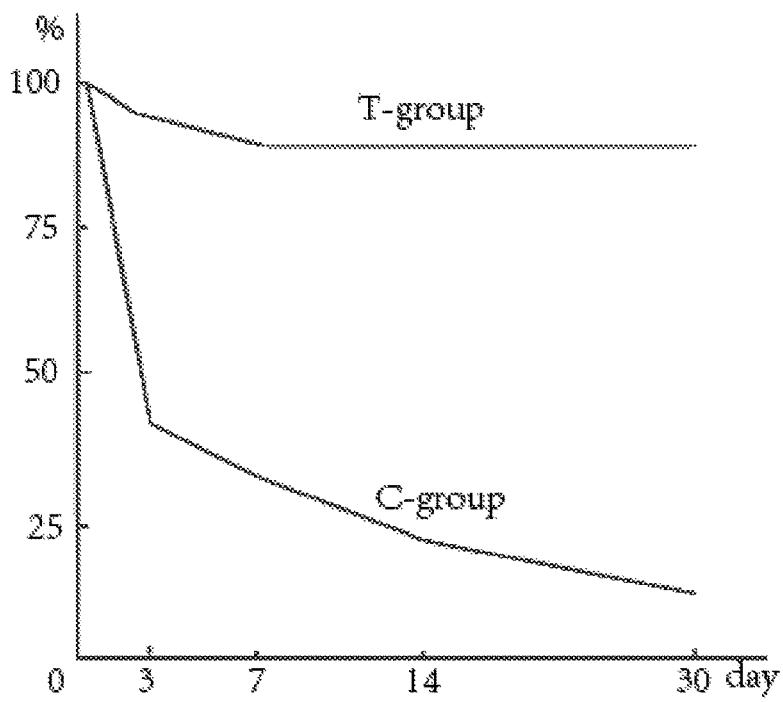
FIG. 5 is a survival curve of sub-acute liver failure treatment group and control group of rats.

FIG. 5 is the survival curve of rats in treatment group and control group, showing survival rate of both groups. The survival rate of the rats in DLL4 treatment group was 98% at day 3, 90% at day 7, 90% at day 14. Meanwhile, the survival rate of the control group was 20% at day 14. Therefore, the pharmaceutical composition of DLL4 cytokine could improve survival rate and survival time in rescuing sub-acute liver failure rats compared to control group. This shows that the present application has achieved apparent benefit.

Example 6. Injectable Suspension Including DLL4 Cytokine for Rescuing Chronic Liver Failure in Small Animal (Domestic Rabbit) Model Animal model: 40 male adult domestic rabbits weighed 2000-2500 g were randomized into 2 groups with 20 rabbits in each group. Each rabbit received a dose of $CCl_4$ via intraperitoneal injection twice a week for 8 weeks to establish the chronic liver failure model.

Treatment group: DLL4 suspension was given to domestic rabbits with successfully induced chronic liver failure at set time via intramuscular injection.

Dose: 5 ml; twice a day.

Control group: the same dose of normal saline (without DLL4) was given to the domestic rabbits.

Both treatment group and control group did not receive other therapy.

Figure 6:
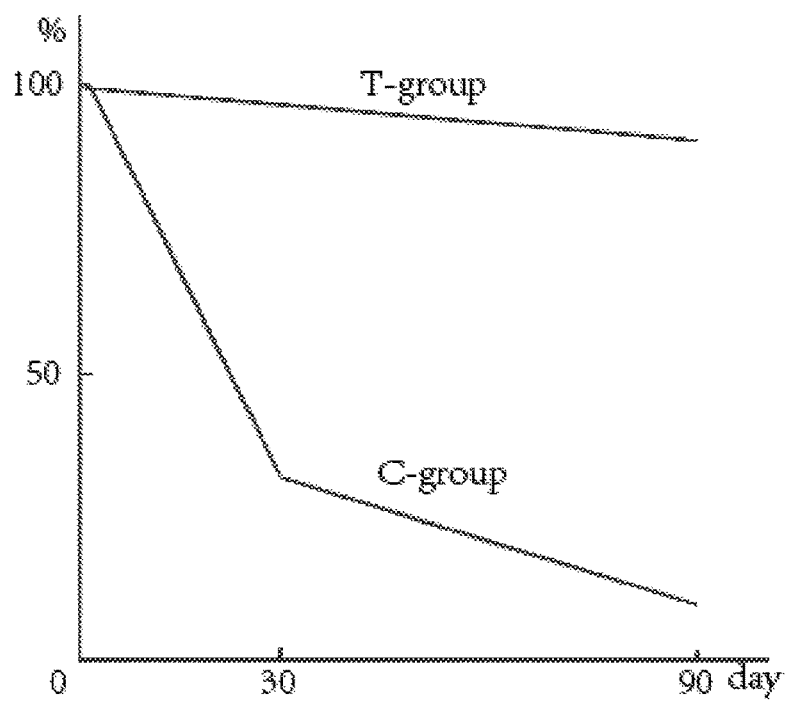
FIG. 6 is a survival curve of chronic liver failure treatment group and control group of domestic rabbits.

FIG. 6 is the survival curve of rabbits in treatment group and control group, showing the survival rate of both groups. The survival rate of the domestic rabbits in treatment group survival rate was 95% at day 30, 90% at day 90. Meanwhile, the survival rate of control group was 40% at day 30, 20% at day 90. Therefore, the pharmaceutical composition of DLL4 cytokine medicine could improve survival rate and survival time in rescuing chronic liver failure domestic rabbits compared to control group. This shows that the present application has achieved apparent benefit.

Example 7. Injectable Suspension Including DLL4 Cytokine for Rescuing Acute-on-Chronic Liver Failure in Small Animal (Mouse) Model Animal model: 100 male adult mice weighed 20-25 g were randomized into 2 groups with 50 mice in each group. Each mouse received a small dose of $CCl_4$ via intraperitoneal injection to establish cirrhosis model. The cirrhosis mice received a dose of D-gal via intraperitoneal injection to induce acute liver failure.

Treatment group: DLL4 suspension was given to mice via intraperitoneal injection at set time.

Dose: 1 ml; twice a day.

Control group: the same dose of normal saline (without DLL4) was given to the mice.

Both treatment group and control group did not receive other therapy.

Figure 7:
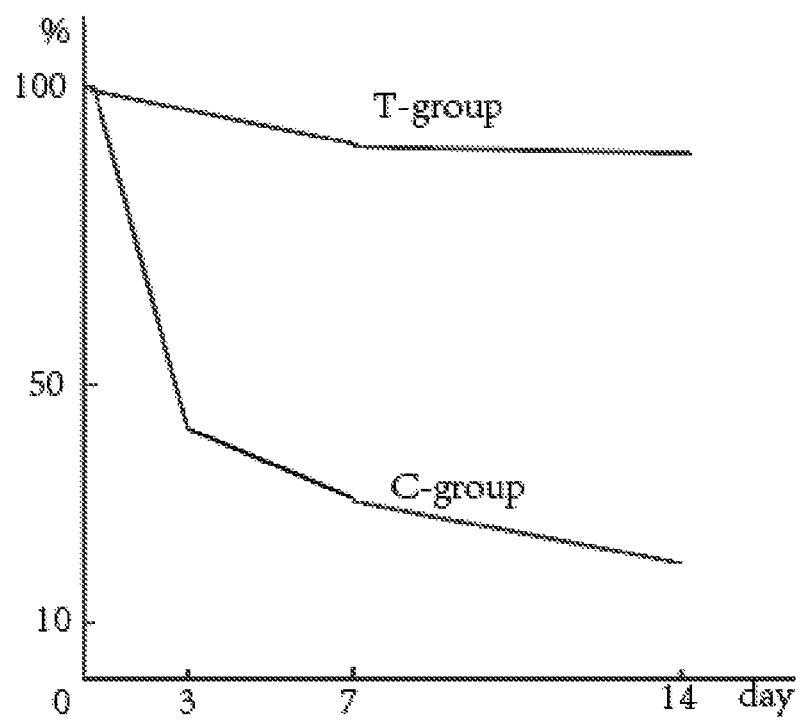
FIG. 7 is a survival curve of acute-on-chronic liver failure treatment group and control group of mice.

FIG. 7 is the survival curve of mice in treatment group and control group, showing survival rate of both groups. The survival rate of mice in the treatment group was 98% at day 3, 94% at day 7, 88% at day 14. Meanwhile, the survival rate of the control group was 25% at day 14. Therefore, the pharmaceutical composition of DLL4 cytokine could improve survival rate and survival time in rescuing acute-on-chronic liver failure mice compared to control group. This shows that the present application has achieved apparent benefit.

Specific embodiments have been described above with reference to the accompanying drawings. However, the present application is not limited to the above specific embodiments. The above specific embodiments are merely illustrative and should not be considered as limiting. It should be noted that, upon reading the above disclosure, a person skilled in the art can make various other changes or modifications without departing from the scope of the appended claims.

What is claimed is:

1. A method of treating liver failure in a subject, comprising administering a therapeutically effective amount of a pharmaceutical composition to the subject, wherein the pharmaceutical composition comprises a human delta like ligand 4 (DLL4) cytokine as set forth in SEQ ID NO: 1.

2. The method according to claim 1, wherein the pharmaceutical composition further comprises a pharmaceutically acceptable excipient, an antioxidant and a carrier.

3. The method according to claim 2, wherein the pharmaceutical composition is in a form of an injection, a lyophilized powder injection or an injectable suspension.

4. The method according to claim 1, wherein the pharmaceutical composition has a storage and transportation temperature between 2° C. and 8° C., and a humidity between 45% and 75%.

5. The method according to claim 1, wherein the liver failure is sub-acute liver failure, chronic liver failure or acute-on-chronic liver failure.

6. The method according to claim 1, wherein the liver failure is fulminant hepatic failure.

* * * * *